United States Patent
Zielenski et al.

(10) Patent No.: US 7,491,495 B2
(45) Date of Patent: Feb. 17, 2009

(54) ADSORPTION OF NUCLEIC ACIDS TO A SOLID PHASE

(75) Inventors: Ralf Zielenski, Benediktbeuern (DE); Klaus Geissler, Oberhausen (DE); Thomas Walter, Penzberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 661 days.

(21) Appl. No.: 11/061,948

(22) Filed: Feb. 18, 2005

(65) Prior Publication Data

US 2005/0214926 A1    Sep. 29, 2005

(30) Foreign Application Priority Data

Feb. 20, 2004  (EP)  ................................. 04003898

(51) Int. Cl.
*C12Q 1/68* (2006.01)
*C07H 19/00* (2006.01)
*C07H 21/00* (2006.01)

(52) U.S. Cl. .......................... 435/6; 536/22.1; 536/25.4
(58) Field of Classification Search .................... 435/6; 536/25.4
See application file for complete search history.

(56) References Cited

U.S. PATENT DOCUMENTS

| | | | | |
|---|---|---|---|---|
| 5,075,430 A | * | 12/1991 | Little | 536/25.41 |
| 5,124,444 A | * | 6/1992 | Van Ness et al. | 536/25.42 |
| 5,130,423 A | * | 7/1992 | Van Ness et al. | 536/25.42 |
| 5,155,018 A | * | 10/1992 | Gillespie et al. | 536/23.1 |
| 5,234,809 A | * | 8/1993 | Boom et al. | 435/91.2 |
| 5,637,687 A | * | 6/1997 | Wiggins | 536/25.4 |
| 5,783,686 A | * | 7/1998 | Gonzalez | 536/25.4 |
| 5,981,235 A | * | 11/1999 | Shultz et al. | 435/91.1 |
| 6,111,096 A | * | 8/2000 | Laugharn et al. | 204/601 |
| 6,120,985 A | * | 9/2000 | Laugharn et al. | 435/1.3 |
| 6,180,778 B1 | * | 1/2001 | Bastian et al. | 536/25.4 |
| 6,218,531 B1 | * | 4/2001 | Ekenberg | 563/25.41 |
| 6,291,166 B1 | * | 9/2001 | Gerdes et al. | 435/6 |
| 6,727,067 B2 | * | 4/2004 | Russman et al. | 435/6 |
| 6,821,757 B2 | * | 11/2004 | Sauer et al. | 435/91.1 |
| 2001/0021518 A1 | * | 9/2001 | Goudsmit et al. | 435/91.2 |
| 2006/0134626 A1 | * | 6/2006 | Chen | 435/6 |
| 2007/0080316 A1 | * | 4/2007 | Sauer et al. | 252/62.51 R |

FOREIGN PATENT DOCUMENTS

| | | |
|---|---|---|
| EP | 0389063 B1 | 9/1990 |
| WO | WO 95/04140 | 2/1995 |
| WO | WO 99/58664 | 11/1999 |
| WO | WO 02/48164 A2 | 6/2002 |
| WO | WO 02/48164 A3 | 6/2002 |

OTHER PUBLICATIONS

Vogelstein et al., Preparative and analytical purification of DNA from agarose. PNAS 76(2) : 615-619 (1979).*
Jakobi et al. Filtered supported preparation of Λ phage DNA. Analytical Biochemistry 175 :196-201 (1988).*
Marko et al. A procedure for the large-scale isolation of highly purified plasmid DNA using alkaline extraction and binding to glass powder. Analytical Biochermistry 121 : 382-387 (1982).*
Boom et al. Rapid and simple method for purification of nucleic acids. J'. of Clinical Microbiology 28(3) : 495-503 (1990).*
Yamada et al., A new method for extracting DNA or RNA for polymerase chain reaction. J. of Virological Mrethods 27 : 203-210 (1990).*
Carter et al.,. An inexpensive and simple method for DNA purifications on silica particles. Nucleic Acids Research 21 (4) : 1044 (1993).*

* cited by examiner

*Primary Examiner*—Ethan Whisenant
(74) *Attorney, Agent, or Firm*—Marilyn Amick; Roche Diagnostics Operations, Inc.

(57) ABSTRACT

The present invention is directed to a method for adsorbing, i.e. non-covalently binding, nucleic acids to a solid phase using a two-step procedure. Furthermore, the present invention pertains to a method for isolating nucleic acids from a biological sample. In the first step of the procedure, lysis is effected by mixing the biological sample with an aqueous lysis buffer containing a chaotropic agent and incubating the mixture; in the second step, the concentration of the chaotropic agent in the mixture is increased and the mixture is contacted with the solid phase, whereby the nucleic acids in the liquid phase is adsorbed to the solid phase.

19 Claims, 5 Drawing Sheets

ADSORPTION OF NUCLEIC ACIDS TO A SOLID PHASE

FIELD OF THE INVENTION

The present invention is directed to a method for adsorbing, i.e. non-covalently binding, a nucleic acid to a solid phase. Furthermore, the present invention pertains to a method for isolating a nucleic acid from a biological sample.

BACKGROUND

Many biological substances, especially nucleic acids, present special challenges in terms of isolating them from their natural environment. On the one hand, they are often present in very small concentrations and, on the other hand, they are often found in the presence of many other solid and dissolved substances e.g. after lysis of cells. This makes them difficult to isolate or to measure, in particular in biospecific assays which allow the detection of specific nucleic acids, or the detection of specific properties of a nucleic acid. Such biospecific assays play a major role in the field of diagnostics and bioanalytics in research and development. Examples for biospecific assays are hybridisation assays, immuno assays and receptor-ligand assays. Hybridisation assays use the specific base-pairing for the molecular detection of nucleic acid analytes e.g. RNA and DNA. Hence, oligonucleotide probes with a length of 18 to 20 nucleotides may enable the specific recognition of a selected complementary sequence e.g. in the human genome. Another assay which entails the selective binding of two oligonucleotide primers is the polymerase chain reaction (PCR) described in U.S. Pat. No. 4,683,195. This method allows the selective amplification of a specific nucleic acid region to detectable levels by a thermostable polymerase in the presence of desoxynucleotide triphosphates in several cycles.

As described above, before the nucleic acids may be analyzed in one of the above-mentioned assays or used for other processes, they have to be isolated or purified from biological samples containing complex mixtures of different components as e.g. proteinaceous and non-proteinaceous components. Often, for the first steps, processes are used which allow the enrichment of the component of interest, i.e. the nucleic acids. Frequently, these are contained in a bacterial cell, a fungal cell, a viral particle, or the cell of a more complex organism, such as a human blood cell or a plant cell. Nucleic acids as a component of interest can also be called a "target component".

To release the contents of said cells or particles, they may be treated with enzymes or with chemicals to dissolve, degrade or denature the cellular walls and cellular membranes of such organisms. This process is commonly referred to as lysis. The resulting solution containing such lysed material is referred to as lysate. A problem often encountered during the lysis is that other enzymes degrading the target component, e.g. desoxyribonucleases or ribonucleases degrading nucleic acids, come into contact with the target component during lysis. These degrading enzymes may also be present outside the cells or may have been spatially separated in different cellular compartments before the lysis and come now into contact with the target component. Other components released during this process may be e.g. endotoxins belonging to the family of lipopolysaccharides which are toxic to cells and can cause problems for products intended to be used in human or animal therapy.

In the next steps of the sample preparation which follow on the lysis step, the nucleic acids are further enriched. Nucleic acids are normally extracted from the complex lysis mixtures before they are used in a probe-based assay. There are several methods for the extraction of nucleic acids. Sequence-dependent or biospecific methods include, e.g., affinity chromatography or hybridisation to immobilised probes. Sequence-independent or physico-chemical methods include, e.g., liquid-liquid extraction with phenol-chloroform, precipitation with pure ethanol or isopropanol, extraction with filter paper, extraction with micelle-forming agents as cetyl-trimethyl-ammonium-bromide, binding to immobilized, intercalating dyes such as acridine derivatives, adsorption to substrates such as silica gel or diatomic earths, adsorption to magnetically attractable glass particles (MGP) or organo silane particles under chaotropic conditions. Direct binding of the nucleic acids to a substrate such as a material with a silica surface is preferred because among other reasons the nucleic acids do not have to be modified and even native nucleic acids can be bound.

Particularly interesting for extraction purposes is the adsorption of nucleic acids to a glass surface although other surfaces are possible.

Nucleic acids which are set free, e.g. by way of cell lysis and/or lysis of cellular organelles such as mitochondria, plastids, nuclei or other nucleic acid-containing organelles, can be purified by way of binding to a solid phase such as a mineral substrate, washing said mineral substrate with the bound nucleic acids and releasing said nucleic acids from said mineral substrate.

Adsorption of nucleic acids to glass particles or silica particles in the presence of chaotropic salts is known to the art (Vogelstein, B., and Gillespie, D., Proc. Natl. Acad. Sci. USA 76 (1979) 615-619) and provide the basis for chromatographic purification and separation processes for nucleic acids. Also known to the art are methods to isolate and purify RNA and DNA from lysates using high concentrations of chaotropic salts, e.g. sodium iodide, sodium perchlorate and guanidine thiocyanate (Boom, R., et al., J. Clin. Microbiol. 28 (1990) 495-503; Yamada, O., et al., J. Virol. Methods 27 (1990) 203-209). The purification of plasmid DNA from bacteria on glass dust in the presence of sodium perchlorate is described in Marko, M. A., et al., Anal. Biochem. 121 (1982) 382-387. In DE 37 24 442, the isolation of single-stranded M13 phage DNA on glass fiber filters by precipitating phage particles using acetic acid and lysis of the phage particles with perchlorate is described. The nucleic acids bound to the glass fiber filters are washed and then eluted with a methanol-containing Tris/EDTA buffer. A similar procedure for purifying DNA from lambda phages is described in Jakobi, R., et al., Anal. Biochem. 175 (1988) 196-201. The procedure entails the selective binding of nucleic acids to glass surfaces in chaotropic salt solutions and separating the nucleic acids from contaminants such as agarose, proteins or cell residue. To separate the glass particles from the contaminants, the particles may be either centrifuged or fluids are drawn through glass fiber filters. This is a limiting step, however, that prevents the procedure from being used to process large quantities of samples.

The use of magnetic particles to immobilize nucleic acids after precipitation by adding salt and ethanol is more advantageous and described e.g. in: Alderton, R. P., et al., Anal. Biochem. 201 (1992) 166-169 and WO 91/00212. In this procedure, the nucleic acids are agglutinated along with the magnetic particles. The agglutinate is separated from the original solvent by applying a magnetic field and performing a wash step. After one wash step, the nucleic acids are dissolved in a Tris buffer. This procedure has a disadvantage, however, in that the precipitation is not selective for nucleic acids. Rather, a variety of solid and dissolved substances are agglutinated as well. As a result, this procedure can not be used to remove significant quantities of any inhibitors of specific enzymatic reactions that may be present. Magnetic, porous glass is also available on the market that contains magnetic particles in a porous, particular glass matrix and is covered with a layer containing streptavidin. This product can be used to isolate biological materials, e.g., proteins or nucleic acids, if they are modified in a complex preparation step so that they bind covalently to biotin. Magnetizable particular adsorbents proved to be very efficient and suitable for automatic sample preparation. Ferrimagnetic and ferromagnetic as well as superparamagnetic pigments are used for this purpose. The most preferred MGPs are those described in WO 01/37291.

Purification of a nucleic acid by way of adsorbing the same to a substrate such as a mineral substrate in the presence of high concentration of salts is also applied to other complex mixtures. Examples therefor are known to the person skilled in the art of molecular biology and include reaction mixtures following, e.g., in-vitro synthesis of nucleic acids such as PCR, restriction enzyme digestions, ligation reactions, etc. In Vogelstein, B., and Gillespie, D., Proc. Natl. Acad. Sci. USA 76 (1979) 615-619, for instance, a procedure for binding nucleic acids from agarose gels in the presence of sodium iodide to ground flint glass is proposed. Another application for purification of a nucleic acid by way of adsorbing the same to a substrate such as a mineral substrate in the presence of a high concentration of salts is the removal of pyrogenic contaminants which may have copurified with the nucleic acid.

The mechanism by which nucleic acids bind to the mineral support in the presence of chaotropic agents is not entirely clear. It is hypothesized that the interaction between the nucleic acids and the solvent is influenced such that the nucleic acids adsorb to the mineral support and denaturate. In the presence of high concentrations of chaotropic agents the reaction is almost quantitative. The adsorbed nucleic acids can be eluted by applying to the mineral support buffers of low ionic strength.

U.S. Pat. No. 5,808,041 discloses methods for isolating nucleic acids with lengths greater than about 50 bases from certain biological samples. An aequous lysate containing chaotropic ions at a concentration above about 2 M is produced and the nucleic acids are adsorbed from the lysate to silica material (also referred to as "binding"). A slurry or resin comprising silica material and chaotropic salts is added to the biological material thus resulting in a one-step lysis and binding procedure. The methods for lysing a biological sample disclosed in the document include lysis of bacteria using alkali hydroxide and SDS, lysis of M13 or lambda phages by incubating the phages in the presence of 2.8 M guanidinium, and lysis of fresh or frozen tissue by incubating the tissue in the presence of 2.8 M guanidinium. Additionally, N-laurylsarcosine is used to aid lysing.

EP 0 389 063 and EP 0 819 696 disclose the method of purifying a nucleic acid by way of mixing in a liquid phase material containing the nucleic acid with a chaotropic substance and a nucleic acid binding solid phase. Thus, the procedures disclosed in the documents also represent one-step lysis and binding procedures. Following lysis and binding, the solid phase with bound nucleic acid is separated from the liquid phase. Following a washing step the nucleic acid is eluted from the solid phase. The documents disclose a lysis buffer containing about 10 M guanidinium thiocyanate, about 2% TRITON X-100 (Rohn & Haas Co.), about 0.1 M Tris salt, and about 50 µM EDTA. Another lysis buffer further contains 40% weight by volume dextrane sulfate. Another lysis buffer contains about 10 M guanidinium thiocyanate and about 50 µM EDTA. Other lysis buffers are disclosed in the documents that contain as a chaotropic substance potassium iodide or sodium iodide at a concentration of about 3 M, or potassium or sodium iodide in combination with 1 M or 8 M urea. Lysis of a biological sample is effected by way of incubating the sample with a lysis buffer, whereby 50 volume parts of the biological sample were mixed with 900 volume parts of a lysis buffer and 40 volume parts of a silica coarse. As an alternative to using silica coarse, other procedures are described wherein silica filter material is used.

EP 0 658 164 describes methods for the chromatographic purification of nucleic acids by way of chromatographic purification. Particularly, a two-step procedure comprising a first lysis step and a second binding step is described. In the first step (lysis), the biological sample is mixed with a chaotropic agent whereby the concentration of the chaotropic agente in the mixture is between about 2 M and about 4 M. Optionally, the mixture additionally contains phenol, chloroform or ether. Optionally, the mixture additionally contains a detergent. A protease is added and the mixture is incubated. In the second step (binding), an alcohol is added and the resulting mixture is contacted with the nucleic acid-binding solid phase.

SUMMARY OF THE INVENTION

The present invention is directed to a method for adsorbing a nucleic acid from a biological sample to a solid phase comprising the steps of (a) providing an aequous lysis buffer that contains a chaotropic agent; (b) mixing the lysis buffer with the biological sample, whereby the concentration of the chaotropic agent in the mixture is between 1 M and 4 M, and incubating the mixture; (c) dissolving an additional amount of chaotropic agent in or adding an aequous solution containing additional chaotropic agent to the mixture of step (b), thereby increasing the concentration of the chaotropic agent in the mixture by more than 0.5 M; and (d) contacting the mixture of step (c) with the solid phase, thereby adsorbing the nucleic acid from the mixture to the solid phase.

The present invention is further directed to a method to isolate a nucleic acid from a biological sample comprising the steps of (a) providing an aequous lysis buffer that contains a chaotropic agent; (b) mixing the lysis buffer with the biological sample, whereby the concentration of the chaotropic agent in the mixture is between 1 M and 4 M, and incubating the mixture; (c) dissolving an additional amount of chaotropic agent in or adding an aequous solution containing additional chaotropic agent to the mixture of step (b), thereby increasing the concentration of the chaotropic agent in the mixture by more than 0.5 M; (d) providing a solid phase and contacting the mixture of step (c) with the solid phase, thereby adsorbing the nucleic acid from the mixture to the solid phase; (e) separating the solid phase from the liquid phase; and (g) eluting the nucleic acid from the solid phase thereby isolating the nucleic acid.

DETAILED DESCRIPTION OF THE INVENTION

The methods of the state of the art have certain disadvantages. Therefore, it was the object of the present invention to provide an alternative method of preparing a biological sample containing a nucleic acid and adsorbing from the preparation the nucleic acid to a solid phase. It was another object of the invention to overcome the need for alcohol during the adsorption step as alcohol is a flammable substance and therefore it is desired to restrict its use.

In the present document it is understood that the term "a nucleic acid" denotes at least one nucleic acid. Furthermore, the term "a nucleic acid" also may indicate a mixture of nucleic acids. The terms "solid phase" and "substrate" denotes a substance which is substantially insoluble in an aequous solution and on which a nucleic acid in an aequous solution of high ionic strength can adsorb when the substance is added. Examples therefore are porous or non-porous mineral particles such as silica, glass, quartz, zeolites or mixtures thereof. Also, the term "substrate" encompasses magnetically attractable particles coated with silica, glass, quartz, or zeolites. Further, it is understood that a substrate in the form of "powder" or "powdered" material refers to finely divided material which, when dispersed in a liquid phase such as a liquid organic compound or an aequous solution, produces a suspension. The term "powder" or "powdered" material is intended to include tablets, in which the powdered material has been aggregated, but still yields a suspension when combined with a liquid phase such as an aequous solution. Further, it is understood that the terms "high ionic strength" and "high concentration" mean the ionic strength or concentration in an aequous solution that results from dissolved salts in concentrations equal to or greater than about 1 M. Preferred are chaotropic salts in concentrations of 1 to 10 M.

The inventors surprisingly found that performing a two-step lysis and binding procedure is advantageous, whereby in the first step lysis is effected by mixing the biological sample with an aequous lysis buffer containing a chaotropic agent and incubating the mixture; in the second step, the concentration of the chaotropic agent in the mixture is increased and the mixture is contacted with a solid phase capable of binding nucleic acids, whereby the nucleic acid in the liquid phase is adsorbed to the solid phase.

A first embodiment of the invention is therefore a method for adsorbing a nucleic acid from a biological sample to a solid phase, comprising the steps of (a) providing an aequous lysis buffer that contains a chaotropic agent; (b) mixing the lysis buffer with the biological sample, whereby the concentration of the chaotropic agent in the mixture is between 1 M and 4 M, and incubating the mixture; (c) dissolving an additional amount of chaotropic agent in or adding an aequous solution containing additional chaotropic agent to the mixture of step (b), thereby increasing the concentration of the chaotropic agent in the mixture by more than 0.5 M; (d) contacting the mixture of step (c) with the solid phase, thereby adsorbing the nucleic acid from the mixture to the solid phase.

A second embodiment of the invention is a method to isolate a nucleic acid from a biological sample, comprising the steps of (a) providing an aequous lysis buffer that contains a chaotropic agent; (b) mixing the lysis buffer with the biological sample, whereby the concentration of the chaotropic agent in the mixture is between 1 M and 4 M, and incubating the mixture; (c) dissolving an additional amount of chaotropic agent in or adding an aequous solution containing additional chaotropic agent to the mixture of step (b), thereby increasing the concentration of the chaotropic agent in the mixture by more than 0.5 M; (d) providing a solid phase and contacting the mixture of step (c) with the solid phase, thereby adsorbing the nucleic acid from the mixture to the solid phase; (e) separating the solid phase from the liquid phase; (f) optionally washing the solid phase of step with a washing buffer; (g) eluting the nucleic acid from the solid phase thereby isolating the nucleic acid; (h) optionally precipitating the nucleic acid of step (g) from the eluate and isolating the precipitated nucleic acid.

Many procedures for isolating nucleic acids from their natural environment have been proposed in recent years by the use of their binding behavior to substrates such as glass surfaces. It is common to use chaotropic agents such as, e.g., guanidine thiocyanate under high salt conditions. A high concentration of a chaotropic agent changes the bulk properties of water (Cacace, M. G., et al. Quarterly Review of Biophysics (1997) 30:241-277).

Certain ions in water will tend to increase hydrophobic interactions, while other ions will decrease hydrophobic interactions. Which ions have a tendency to which effect is described by what is called a Hofmeister series. The series is as follows:

Cations:
$NH_4^+ > Rb^+ > K^+ > Na^+ > Cs^+ > Li^+ > Mg^{2+} > Ca^{2+} > Ba^{2+} >$ guanidinium Anions:
$PO_4^{3-} > SO_4^{2-} > HPO_4^{2-} >$ acetate$>$citrate$>$tartrate$> Cl^- > Br^- > NO_3^- > ClO_3^- > ClO_4^- > I^- > SCN^-$ Ions on the left are said to be "kosmotropic" and increase the strength of hydrophobic interactions and thus will precipitate or "salt out" proteins at a high concentrations. Ions on the right are "chaotropic" and tend to weaken hydrophobic interactions. The Hofmeister series explains why guanidinium is a protein denaturant. It weakens hydrophobic interactions causing proteins to denature. In contrast, $(NH_4)_2SO_4$ will dissociate into $NH_4^+$ and $SO_4^{2-}$ ions. Both of these ions are kosmotropic, and the effect of each is independent and additive. This makes $(NH_4)_2SO_4$ a versatile precipitant which is widely used in protein purification procedures. NaCl is in the middle of the series, that is it is neither kosmotropic nor chaotropic.

It was found by the inventors that for preparing a biological sample containing a nucleic acid and adsorbing from the preparation the nucleic acid to a solid phase advantageously a two-step lysis and binding method is applied. In the first step (lysis) the concentration of the chaotropic agent is lower than in the second step (binding). During the lysis step, that is to say in the mixture of the biological sample and the lysis buffer the preferred concentration of the chaotropic agent is between 1 M and 4 M. A first preferred embodiment of the invention is therefore a method for adsorbing a nucleic acid from a biological sample to a solid phase, comprising the steps of (a) providing an aequous lysis buffer that contains a chaotropic agent; (b) mixing the lysis buffer with the biological sample, whereby the concentration of the chaotropic agent in the mixture is between 1 M and 4 M, and incubating the mixture; (c) dissolving an additional amount of chaotropic agent in or adding an aequous solution containing additional chaotropic agent to the mixture of step (b), thereby increasing the concentration of the chaotropic agent in the mixture by more than 0.5 M; (d) contacting the mixture of step (c) with the solid phase, thereby adsorbing the nucleic acid from the mixture to the solid phase.

It is preferred that the chaotropic agent is a chaotropic salt. It is more preferred that the chaotropic agent is selected from the group consisting of guanidinium hydrochloride, guanidinium thiocyanate, guanidinium isothiocyanate, an alkali iodide, and an alkali perchlorate. Preferably, the alkali iodide is KI or NaI. Preferably, the alkali perchlorate is $NaClO_4$ or $KClO_4$. Mixtures of these compounds as well as mixtures of these compounds with urea are also possible.

Depending on the chaotropic agent used, the optimal concentration thereof in the mixture of step (b) may vary. E.g., to obtain a comparable chaotropic effect using guanidinium hydrochloride or guanidinium thiocyanate different concentrations in the indicated range of between 1 M and 4 M must be selected. The principle underlying this difference is that the guanidinium thiocyanate salt when dissolved in water dissociates to result in two chaotropic ions, whereas dissociated guanidinium hydrochloride results in only one chaotropic ion. It is therefore preferred that in the mixture of step (b) the concentration of the chaotropic agent is between 1 M and 2 M. It is more preferred that in the mixture of step (b) the concentration of the chaotropic agent is between 1.5 M and 2 M. It is even more preferred that in the mixture of step (b) the concentration of the chaotropic agent is about 2 M. Depending on the chaotropic agent used it is also preferred that in the mixture of step (b) the concentration of the chaotropic agent is between 2 M and 4 M. It is more preferred that in the mixture of step (b) the concentration of the chaotropic agent is between 2.5 M and 3 M. It is even more preferred that in the mixture of step (b) the concentration of the chaotropic agent is about 3 M.

In this regard it is the general understanding of the skilled artisan that the word "about" in combination with a numerically quantified value means that this value may be subject to vartiation, whereby the desired technical effect which is described or defined by the value remains unchanged. Generally, "about" is understood to imply a variation of 5%. For example, a value of about 100 comprises the values between 95 and 105.

Guanidinium and thiocyanate ions are classified in the Hofmeister series as having enhanced chaotropic properties over, e.g. potassium or sodium cations, or iodide or chlorate anions, respectively. It is thus also preferred that in the mixture of step (b) the concentration of the chaotropic agent is between 2 M and 4 M.

In the second step (binding) the concentration of chaotropic agent in the mixture is increased by adding additional chaotropic agent to the mixture of step (b). As indicated for step (c) there are several ways to achieve the desired increase. It is possible to add the chaotropic agent as solid matter to the mixture of step (b) and dissolve the chaotropic agent. Alternatively, an aequous solution of the chaotropic agent is prepared and added to the mixture of step (b). Preferably, the aequous solution contains further ingredients such as a buffer salt, a detergent or both. An example for such an aequous solution is the binding buffer described in Examples 2, 3 and 4.

The concentration of the chaotropic agent in the mixture of step (c) is increased by more than 0.5 M. It is preferred, therefore, that step (c) comprises dissolving an additional amount of chaotropic agent in or adding an aequous solution containing additional chaotropic agent to the mixture of step (b), thereby increasing the concentration of the chaotropic agent in the mixture to a value between 1.5 M and 10 M. It is noted that additional chaotropic agent can be added as solid matter to the mixture of step (b) until saturation in the mixture is reached. Thus, it is further preferred that step (c) comprises dissolving an additional amount of chaotropic agent in the mixture of step (b), thereby saturating the mixture with the chaotropic agent. It is preferred that in step (c) the concentration of the chaotropic agent in the mixture is increased by between 0.5 M and 6 M. It is more preferred that in step (c) the concentration of the chaotropic agent in the mixture is increased by between 0.5 M and 4 M. It is even more preferred that in step (c) the concentration of the chaotropic agent in the mixture is increased by between 0.5 M and 3 M. It is even more preferred that in step (c) the concentration of the chaotropic agent in the mixture is increased by between 0.5 M and 2 M. It is even more preferred that in step (c) the concentration of the chaotropic agent in the mixture is increased by between 0.5 M and 1.5 M. It is even more preferred that in step (c) the concentration of the chaotropic agent in the mixture is increased by between 0.5 M and 1 M.

In detail, the procedure for binding a (at least one) nucleic acid (also referred to as target nucleic acid) to a substrate such as, e.g., silica particles, silica fibers, glass filter or glass particles can be described as follows. According to the invention it is performed in the presence of chaotropic salts with a concentration of between 1.5 M and 10 M, and preferably between 2 M and 6 M.

DNA or RNA bind to material with a glass surface under these conditions i.e. in the presence of certain concentrations of a chaotropic agent. To bring the lysate in contact with the substrate, i.e. the material with an affinity to nucleic acids, the lysate is mixed with the substrate and incubated for a period of time sufficient for the binding to occur. In case the substrate is a filter comprising e.g. glass, silica, or quartz fibers, the lysate (i.e. the mixture of step (c)) can be passed through the filter by gravitational pull, by applying pressure or by applying suction. While passing through the filter, the nucleic acid in the liquid phase comes in contact with the solid phase and is adsorbed thereto. Experts are usually familiar with the duration of the incubation of the liquid phase and the solid phase. The incubation can be optimized by determining the quantity of immobilized biological material on the surface at different points in time. Incubation times of between 10 seconds and 30 minutes can be appropriate for nucleic acids.

It is further preferred to use in the procedures for binding a nucleic acid to a solid phase or for isolating a nucleic acid from a biological sample an enzyme with proteolytic activity when lysing a biological sample in order to set free the nucleic acids. The term "enzyme with proteolytic activity" is understood to encompass a protease or a mixture of proteases to rapidly degrade in the biological sample nucleic acid degrading enzymes or other unwanted proteins. In the present context, the term "protease" is intended to mean any hydrolase, peptidase, proteinase or enzyme having proteolytic activity (i.e. hydrolases acting on peptide bonds) as comprised in EC 3.4-3.11 and any modification thereof, which modification have retained the activity of the enzyme. The enzyme with proteolytic activity may be isolated from animal tissue, plant tissue, a microorganism, or may be obtained by recombinant means.

Therefore, it is preferred that the lysis buffer of step (a) contains an enzyme with proteolytic activity. It is more preferred that the enzyme with proteolytic activity is selected from the proteases as comprised in EC 3.4-3.11. It is even more preferred that the enzyme with proteolytic activity is selected from the group consisting of Achromopeptidase, Aminopeptidase, Ancrod, Angiotensin Converting Enzyme, Bromelain, Calpain, Calpain I, Calpain II, Carboxypeptidase A, Carboxypeptidase B, Carboxypeptidase G, Carboxypeptidase P, Carboxypeptidase W, Carboxypeptidase Y, caspase, caspase 1, caspase 2, caspase 3, caspase 4, caspase 5, caspase 6, caspase 7, caspase 8, caspase 9, caspase 10, caspase 13, Cathepsin B, Cathepsin C, Cathepsin D, Cathepsin G, Cathepsin H, Cathepsin L, Chymopapain, Chymase, alpha-Chymotrypsin, Clostripain, Collagenase, Complement C1r, Complement C1s, Complement Factor D, Complement factor I, Cucumisin, Dipeptidyl peptidase IV, leukocyte Elastase, pancreatic Elastase, Endoproteinase Arg-C, Endoproteinase Asp-N, Endoproteinase Glu-C, Endoproteinase Lys-C, Enterokinase, Factor Xa, Ficin, Furin, Granzyme A, Granzyme B, HIV Protease, IGase, Kallikrein tissue, Leucine Aminopeptidase, cytosolic Leucine aminopeptidase, microsomal Leucine aminopeptidase, Matrix metalloprotease, Methionine Aminopeptidase, Neutrase, Papain, Pepsin, Plasmin, Prolidase, pronase E, Prostate Specific Antigen, Alkalophilic protease from *Streptomyces griseus*, Protease from *Aspergillus*, Protease from *Aspergillus saitoi*, Protease from *Aspergillus sojae*, Alkaline protease from *B. licheniformis*, Alcalase from *B. licheniformis*, Protease from *Bacillus polymyxa*, Protease from *Bacillus* sp, Protease from *Bacillus* sp (esperase), Protease from *Rhizopus* sp., Protease S, Proteasomes, Proteinase from *Aspergillus oryzae*, Proteinase 3, Proteinase A, proteinase K, Protein C, Pyroglutamate aminopeptidase, Renin, Rennin, Streptokinase, subtilisin, Thermolysin, Thrombin, Tissue Plasminogen Activator, Trypsin, Tryptase, and Urokinase. It is even more preferred that the enzyme with proteolytic activity is selected from the group consisting of a caspase, proteinase K, pronase E, Protease from *Bacillus* sp (esperase), and subtilisin. A mixture of at least two different proteases as comprised in EC 3.4-3.11 is also preferred. With regard to the selection of a protease experts are usually familiar with the optimization of lysis buffers. As described in Example 1, the skilled artisan will test for proteolytic activity of a selected protease in a buffer containing a chaotropic agent at different concentrations. A protease active under the chaotropic conditions of a mixture according to step (b) is preferably selected. Optimization of the duration of the incubation with the protease as well as the optimization of the incubation temperature can be performed by the expert. As a parameter, the skilled artisan will determine the quantity of nucleic acid(s) set free from the biological sample into the liquid phase and capable of being bound to the substrate.

It is highly preferred that the lysis buffer of step (a) contains proteinase K. Preferably, the activity of proteinase K in the mixture of step (b) is between 0.1 U/ml and 10 U/ml. It is more preferred that the activity of proteinase K in the mixture of step (b) is between 1 U/ml and 6 U/ml. It is even more preferred that the activity of proteinase K in the mixture of step (b) is between 2 U/ml and 4 U/ml. It is even more preferred that the activity of proteinase K in the mixture of step (b) is about 3 U/ml. In this regard it is understood that the recited activity values of proteinase K reflect activity values determined as described in Example 1.

When lysing a biological sample in order to set free the nucleic acids or when binding the nucleic acid to the solid phase it is further preferred to use a detergent in the procedures, that is to say an anionic, cationic, zwitterionic or non-ionic detergent. Such detergents are well known to the person skilled in the art. Generally, a "detergent" is a surface active agent, also known as a surfactant. A detergent is capable of lowering the surface tension of the medium in which it is dissolved, and/or the interfacial tension with other phases, and, accordingly, is positively adsorbed at the liquid/vapour and/or at other interfaces. Thus, detergents are amphipathic molecules with polar (water soluble) and nonpolar (hydrophobic) domains. They are capable of binding to hydrophobic molecules or molecular domains to confer water solubility. Depending on its ionic characteristics, a detergent can be categorized as an ionic detergent, a non-ionic detergent, and a zwitterionic detergent. Ionic detergents can be further classified into either cationic detergents such as SDS (sodium dodecyl sulfate), LiDS (lithium dodecyl sulfate), or cetyltrimethylammoniumbromide (CTAB), and anionic detergents such as deoxycholic acid, or sodium lauroyl sarcosine. Thus, these are usually highly protein denaturant. Non-ionic detergents such as are less protein denaturant. This is also true for zwitterionic detergents such as CHAPS or Sulphobetaine 14. Zwitterionic compounds, also known as zwitterions, inner salts or dipolar ions are neutral compounds having formal unit electrical charges of opposite sign.

Therefore, it is preferred that the lysis buffer of step (a) contains a detergent. It is more preferred that the lysis buffer of step (a) contains an anionic, cationic, zwitterionic or non-ionic detergent. It is even more preferred that the detergent in the lysis buffer of step (a) is selected from the group consisting of sodium dodecyl sulfate, lithium dodecyl sulfate, cetyltrimethylammoniumbromide, deoxycholic acid, sodium lauroyl sarcosine, TRITON X-100, TWEEN 20 (ICI Americas Inc.), octyl beta-D-glucoside, Nonidet P40, CHAPS or Sulphobetaine 14. However, other detergents are possible. Generally, when using the combination of a chaotropic agent, a detergent and a protease for lysing a biological sample, the skilled artisan selects a detergent and its concentration in the mixture of step (b) on the basis that proteolytic activity is preserved.

Preferably, the solid phase comprises a porous or non-porous mineral substrate selected from the group consisting of silica gel, glass fibers, quartz fibers, and zeolites. Also preferred, the solid phase comprises a porous or non-porous mineral substrate selected from the group consisting of metal oxides, and/or metal mixed oxides, alumina, titania, zirconia, and materials predominantly consisting of glass. It is also preferred that the solid phase comprises a mineral substrate with a particle size of 0.1 µm to 1,000 µm. It is also preferred that the solid phase comprises porous mineral support materials with a pore size of from 2 to 1,000 nm. More preferred, porous or non-porous support materials, especially zeolites, are in the form of loose packings. Even more preferred, the solid phase consists of filter sheets in the form of glass, quartz or ceramic filter sheets, and/or a membrane containing silica gel and/or particles or fibers of mineral supports and fabrics of quartz or glass wool. It is also preferred that the solid phase comprises magnetically attractable particles. More preferred, the magnetically attractable particles are coated with a mineral substrate selected from the group consisting of silica gel, glass, quartz, and zeolites. Even more preferred, the substrate comprises magnetic glass particles.

A further embodiment of the invention is a method to isolate a nucleic acid from a biological sample, comprising the steps of (a) providing an aequous lysis buffer that contains a chaotropic agent; (b) mixing the lysis buffer with the biological sample, whereby the concentration of the chaotropic agent in the mixture is between 1 M and 4 M, and incubating the mixture; (c) dissolving an additional amount of chaotropic agent in or adding an aequous solution containing additional chaotropic agent to the mixture of step (b), thereby increasing the concentration of the chaotropic agent in the mixture by more than 0.5 M; (d) providing a solid phase and contacting the mixture of step (c) with the solid phase, thereby adsorbing the nucleic acid from the mixture to the solid phase; (e) separating the solid phase from the liquid phase; (f) optionally washing the solid phase of step with a washing buffer; (g) eluting the nucleic acid from the solid phase thereby isolating the nucleic acid; (h) optionally precipitating the nucleic acid of step (g) from the eluate and isolating the precipitated nucleic acid.

It is preferred that the solid phase comprises a porous or non-porous mineral substrate selected from the group consisting of silica gel, glass fibers, quartz fibers, and zeolites. It is also preferred that the solid phase comprises magnetic glass particles.

It is very much preferred that the chaotropic agent is a chaotropic salt. It is more preferred that the chaotropic agent is selected from the group consisting of guanidinium hydrochloride, guanidinium thiocyanate, guanidinium isothiocyanate, an alkali iodide, and an alkali perchlorate.

It is also preferred that the lysis buffer of step (a) contains an enzyme with proteolytic activity and a detergent. It is very much preferred that the lysis buffer of step (a) contains an enzyme with proteolytic activity. It is more preferred that the enzyme with proteolytic activity is selected from the proteases as comprised in EC 3.4-3.11. It is even more preferred that the enzyme with proteolytic activity is selected from the group consisting of a caspase, proteinase K, pronase E, Protease from *Bacillus* sp (esperase), and subtilisin. A mixture of at least two different proteases as comprised in EC 3.4-3.11 is also preferred. It is also very much preferred that the lysis buffer of step (a) contains an anionic, cationic, zwitterionic or non-ionic detergent. It is even more preferred that the detergent in the lysis buffer of step (a) is selected from the group consisting of sodium dodecyl sulfate, lithium dodecyl sulfate, cetyltrimethylammoniumbromide, deoxycholic acid, sodium lauroyl sarcosine, TRITON X-100, TWEEN 20, octyl beta-D-glucoside, Nonidet P40, CHAPS or Sulphobetaine 14.

It is preferred that the pH value of the mixture of step (b) is between 8.5 and 4. It is more preferred that the pH value of the mixture of step (b) is between 7.5 and 5. It is even more preferred that the pH value of the mixture of step (b) is between 7 and 6. It is even more preferred that the pH value of the mixture of step (b) is about 6.

It is very much preferred that the mixture of step (b) contains the biological sample, guanidinium thiocyanate at a concentration between 1.5 M and 3 M, Tris salt at a concentration of between 20 mM and 40 mM, TRITON X-100 at a concentration of between 5% and 20% volume by volume, and proteinase K, whereby the proteolytic activity of proteinase K in the mixture is between 1 U/ml and 5 U/ml, and whereby the pH of the mixture is between 8.5 and 6.0. In this regard it is understood that the activity of proteinase K is determined as described in Example 1.

It is highly preferred that the mixture of step (b) contains the biological sample, guanidinium thiocyanate at a concentration between 1.5 M and 2.5 M, Tris salt at a concentration of between 20 mM and 30 mM, TRITON X-100 at a concentration of between 5% and 15% volume by volume, and proteinase K, whereby the proteolytic activity of proteinase K in the mixture is between 2 U/ml and 4 U/ml, and whereby the pH of the mixture is between 8.5 and 6.0.

It is highly preferred that the mixture of step (b) contains the biological sample, guanidinium thiocyanate at a concentration of about 2 M, Tris salt at a concentration of about 25 mM, TRITON X-100 at a concentration of about 10% volume by volume, and proteinase K, whereby the proteolytic activity of proteinase K in the mixture is about 3 U/ml, and whereby the pH of the mixture is about 6. Even more preferred is a pH of 6. An example therefor is the lysis mixture (i.e. the mixture according to step (b)) used in Experiment 4 of Example 2.

It is also highly preferred that the mixture of step (b) contains the biological sample, guanidinium hydrochloride at a concentration of about 2.7 M, urea at a concentration of about 5 mM, Tris salt at a concentration of about 5 mM, TRITON X-100 at a concentration of about 9% volume by volume, and proteinase K, whereby the proteolytic activity of proteinase K in the mixture is about 3 U/ml, and whereby the pH of the mixture is between 4.4 and 6.5.

It is also highly preferred that the mixture of step (b) contains the biological sample, guanidinium hydrochloride at a concentration of about 2.4 M, urea at a concentration of about 1.6 mM, Tris salt at a concentration of about 85 mM, EDTA at a concentration of about 88 mM, NaCl at a concentration of about 8 mM, TRITON X-100 at a concentration of about 9% volume by volume, and proteinase K, whereby the proteolytic activity of proteinase K in the mixture is about 3 U/ml, and whereby the pH of the mixture is between 4.4 and 6.5.

It is further preferred that the mixture of step (b) including a protease is incubated for a certain amount of time and at ambient conditions that allow proteolytic activity. It is preferred that the mixture of step (b) is incubated for 10 min to 30 min at a temperature between 20° C. and 75° C., whereby the mixture is agitated. Preferred agitation means is a roller mixer or a thermomixer. The terms "agitation" and "to agitate" are understood as moving the test tube containing the mixture of step (b) as to invert the test tube once a second. The terms also include movements having an equivalent effect with regard to causing turbulence in the mixture of step (b). The degree of agitation can also be influenced by the size of the nucleic acid(s) to be isolated. Too much agitation can lead to shearing forces resulting in size restriction of the nucleic acid molecules in the mixture. Therefore, slower agitation may be selected by the expert.

It is more preferred that the mixture of step (b) is incubated for 30 min at room temperature, whereby the mixture is agitated using a roller mixer. It is even more preferred that the mixture of step (b) is incubated for about 10 to 20 min at a temperature between 50° C. and 75° C., whereby the mixture is agitated using a thermomixer. It is even more preferred that the mixture of step (b) is incubated for 10 min to 20 min at about 56° C., whereby the mixture is agitated using a roller mixer or a thermomixer. It is even more preferred that the mixture of step (b) is incubated for 15 min at 56° C., whereby the mixture is agitated using a roller mixer or a thermomixer. It is also very much preferred that the mixture of step (b) is incubated for 10 min to 20 min at about 72° C., whereby the mixture is agitated using a roller mixer or a thermomixer. It is even more preferred that the mixture of step (b) is incubated for 10 min at 72° C., whereby the mixture is agitated using a roller mixer or a thermomixer.

After adsorbing the nucleic acid(s) from the mixture of step (c) to the solid phase, bound nucleic acid(s) is separated from the liquid phase. This may be achieved in general by gravity or in the convenient case of nucleic acids bound to magnetic glass particles by separating the material bound to the magnetic particles by applying a magnetic field. For instance, the magnetic particles can be pulled to the wall of the vessel in which incubation was performed. The liquid containing the sample contents that were not bound to the magnetic particles can then be removed. The removal procedure used depends on the type of vessel in which incubation was performed. Suitable steps include removing the liquid via pipetting or aspiration.

In case the solid phase is a filter (such as a filter comprising quartz or glass fibers) the mixture of step (c) is preferably passed through the filter. Separation of the liquid phase from the solid phase is then effected by by gravitational pull, by the application of pressure or by the application of suction.

The solid phase with the bound DNA or RNA may then be washed. This step is optional, depending on the nature and the amount of undesired material in the biological sample as well as on the desired purity of the isolated nucleic acid. If a washing step is desired, it is preferred that the solid phase is washed at least once, e.g. with a mixture of 1-90% volume by volume of an alcohol such as isopropyl alcohol or ethanol. Examples for wash solutions are the "Inhibitor Removal Buffer" and the "Wash Buffer" described in Example 2 (A). Generally, a wash solution is used that does not cause the nucleic acid(s) to be released from the surface of the solid phase but that washes away the undesired contaminants as thoroughly as possible. This wash step preferably takes place by incubating the material with the bound nucleic acid(s) with the wash solution. The solid phase is preferably resuspended during this step. In case the solid phase is a filter it is preferred that the wash solution is passed through the filter. The contaminated wash solution is preferably removed just as in the step described above for binding the nucleic acids. It is even more preferred to perform two consecutive washing steps, whereby the first washing step is performed using inhibitor removal buffer and the second washing step is performed using wash buffer. An inhibitor removal buffer is characterized in that it contains a chaotropic agent. Washing with the inhibitor removal buffer removes toxic substances or inhibitors that can interfere with enzymatic reactions such as, e.g. reactions performed by restriction enzyme or polymerases. Washing with washing buffer removes residual chaotropic agent from the bound nucleic acids. After the last wash step, the material can be dried briefly in a vacuum, or the fluid can be allowed to evaporate. A pretreatment step using acetone may also be performed.

Afterwards, the conditions may be reversed, e.g. the salt concentration is decreased to elute the DNA or RNA bound to the material. Elution buffers are known from DE 37 24 442 and Jakobi, R., et al., Anal. Biochem. 175 (1988) 196-201. Elution buffers with a low salt content are in particular buffers with a content of less than 0.2 M. Preferably, the elution buffer contains the substance Tris for buffering purposes. It is very much preferred that the elution buffer is an aequous solution containing a Tris salt, whereby the concentration of the Tris salt is 50 mM. More preferred is an aequous solution containing a Tris salt, whereby the concentration of the Tris salt is 50 mM and the pH is between 6.5 and 8.5. Even more preferred is a pH of 7.5. Also preferred, the elution buffer is demineralized water. The solution containing purified DNA or RNA can now be used for other reactions. Optionally, the nucleic acid(s) can be precipitated from the solution using, e.g., ethanol or isopropanol. The precipitate can also be subjected to further washing steps. Methods of this kind are well known to the skilled artisan and are described in detail in Sambrook, Fritsch & Maniatis, Molecular Cloning, A Laboratory Manual, 3rd edition, CSHL Press, 2001.

The target nucleic acid(s) can be detected and determined. The above-described purification method is preferred, followed by a determination or detection step or purification methods followed by an amplification and determination or detection step. The target nucleic acid or nucleic acids of interest may be contained in a matrix of non-target nucleic acids, and may even be a minor component in said mixture of specific nucleic acids. Suitable DNA detection methods are known to the skilled artisan and are described in standard textbooks as Sambrook, Fritsch & Maniatis, Molecular Cloning, A Laboratory Manual, 3rd edition, CSHL Press, 2001; and Ausubel et al., Current Protocols in Molecular Biology, J. Wiley and Sons, NY, 1987.

There may be also further purification steps before the DNA detection step is carried out as e.g. a precipitation step. The detection methods may include but are not limited to the binding or intercalating of specific dyes as ethidiumbromide which intercalates into the double-stranded DNA and changes its fluorescence thereafter. The purified DNA may also be separated by electrophoretic methods, optionally after a restriction digest, and visualized thereafter. There are also probe-based assays which exploit the oligonucleotide hybridization to specific sequences and subsequent detection of the hybrid. It is also possible to sequence the DNA after further steps known to the skilled artisan. Other methods apply a diversity of DNA sequences to a silicon chip to which specific probes are bound and yield a signal when a complementary sequences bind.

The invention also encompasses the mixture of non-proteinaceous and proteinaceous components comprising nucleic acids whereby the nucleic acids comprise DNA or RNA or both.

The invention also encompasses biological samples, from which nucleic acids are purified, comprising viruses or bacterial cells, as well as isolated cells from multicellular organisms as e.g. human and animal cells such as leucocytes, and immunologically active low and high molecular chemical compounds such as haptens, antigens, antibodies and nucleic acids, blood plasma, cerebral fluid, sputum, stool, biopsy specimens, bone marrow, oral rinses, blood serum, tissues, urine or mixtures thereof. The present invention also encompasses biological samples such as a fluid from the human or animal body; preferably the biological sample is whole blood, blood plasma, blood serum or urine. The whole blood sample is preferably EDTA blood, heparin or citrate blood. The blood plasma is preferably EDTA, heparin or citrate blood plasma. In an embodiment of the invention the biological sample comprises bacterial cells, eukaryotic cells, viruses or mixtures thereof.

It is also preferred that the mixture of nucleic acids and proteinaceous material comprises desoxyribonucleic acid (DNA) or ribonucleic acid (RNA) or both, preferably the DNA or RNA or both is derived from a virus or a (at least one) microorganism. The virus can be hepatitis A virus (HAV), hepatitis B virus (HBV), hepatitis C virus (HCV), the human immunodeficiency virus (HIV), the human papilloma virus (HPV) or parvovirus B19.

It is also preferred that a target nucleic acid component and the other nucleic acids are purified essentially as described above. Then the target nucleic acid component is further manipulated and detected, i.e. it is amplified with the polymerase chain reaction which specifically amplifies target sequences to detectable amounts. Other possible amplification reactions are the ligase Chain Reaction (LCR, Wu, D. Y., and Wallace, R. B., Genomics 4 (1989) 560-569, and Barany, F., Proc. Natl. Acad. Sci. USA 88 (1991) 189-193); Polymerase Ligase Chain Reaction (Barany, F., PCR Methods and Applic. 1 (1991) 5-16); Gap-LCR (WO 90/01069); Repair Chain Reaction (EP 0 439 182), 3SR (Kwoh, D. Y., et al., Proc. Natl. Acad. Sci. USA 86 (1989) 1173-1177; Guatelli, J. C., et al., Proc. Natl. Acad. Sci. USA 87 (1990) 1874-1878; WO 92/08800), and NASBA (U.S. Pat. No. 5,130,238). Further, there are strand displacement amplification (SDA), transciption mediated amplification (TMA), and Q-beta-amplification (for a review see e.g. Whelen, A. C., and Persing, D. H., Annu. Rev. Microbiol. 50 (1996) 349-373; Abramson, R. D., and Myers, T. W., Curr. Opin. Biotechnol. 4 (1993) 41-47).

Particularly preferred is the TAQMAN (Roche Molecular Systems, Inc.) detection method disclosed in WO 92/02638 and the corresponding U.S. Pat. Nos. 5,210,015; 5,804,375; 5,487,972. This method exploits the exonuclease activity of a polymerase to generate a signal. In detail, the target nucleic acid component is detected by a process comprising contacting the sample with an oligonucleotide containing a sequence complementary to a region of the target nucleic acid component and a labelled oligonucleotide containing a sequence complementary to a second region of the same target nucleic acid component sequence strand, but not including the nucleic acid sequence defined by the first oligonucleotide, to create a mixture of duplexes during hybridization conditions, wherein the duplexes comprise the target nucleic acid annealed to the first oligonucleotide and to the labelled oligonucleotide such that the 3'-end of the first oligonucleotide is adjacent to the 5'-end of the labelled oligonucleotide. Then this mixture is treated with a template-dependent nucleic acid polymerase having a 5' to 3' nuclease activity under conditions sufficient to permit the 5' to 3' nuclease activity of the polymerase to cleave the annealed, labelled oligonucleotide and release labelled fragments. The signal generated by the hydrolysis of the labelled oligonucleotide is detected and/or measured. TAQMAN technology eliminates the need for a solid phase bound reaction complex to be formed and made detectable. In more general terms, a procedure for the purification of a target nucleic acid component followed by a detection step is disclosed wherein the amplification and/or detection reaction is a homogeneous solution-phase.

The following examples, references, and figures are provided to aid the understanding of the present invention, the true scope of which is set forth in the appended claims. It is understood that modifications can be made in the procedures set forth without departing from the spirit of the invention.

EXAMPLE 1

Figure 1:
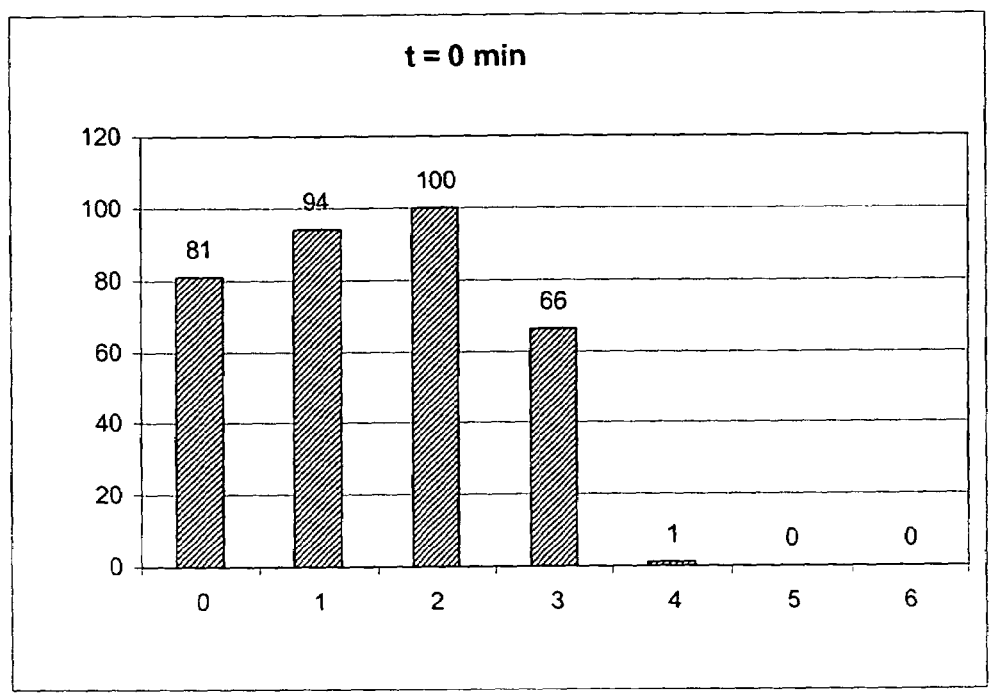
FIG. 1 Activity of proteinase K at t=0 min in relation to varying concentrations of guanidinium thiocyanate (0 min values). The x axis indicates the molar concentration of guanidinium thiocyanate, the y axis indicates the activity of proteinase K in [%].

(A) Incubation of Proteinase K in the Presence of a Chaotropic Agent

10 μl of a 20 mg/ml stock solution of proteinase K (Roche Diagnostics GmbH, Mannheimm, catalogue no. 745723; 90 mg dissolved in 4.5 ml water) was mixed with a chaotropic buffer containing 50 mM Tris-HCl pH 6.0, 1% DTT, 20% TRITON X-100 and x M Guanidinum thiocyanate; x=0, 1, 2, 3, 4, 5, 6). Directly after mixing the proteinase K activity was measured in a first aliquot (10 μl) of the mixture using the assay described below (0 min activity value). 15 min after mixing the proteinase K activity was measured in a second aliquot (10 μl) of the mixture using the assay described below (15 min activity value).

(B) Assay to Determine Proteinase K Activity

10 μl of the proteinase K in chaotropic buffer (see above, (A)) were mixed with assay buffer, that is to say 980 μl 0.2 M Triethanolamin, 0.05% (weight by volume) PEG 6000, 0.1 M Calcium chloride, and 10 μl of a 200 mM substate solution. The substrate was Suc-Ala-Ala-Ala-p-Nitroanilid. The assay buffer was provided in a cuvette. Immediately after mixing the cuvette was placed in a Photometer. Measurements (absorption) were taken over 15 min at 25° C. The activity of proteinase K in the assay buffer was calculated from the kinetics as indicated by a change in absorption at 405 nm.

Figure 2:
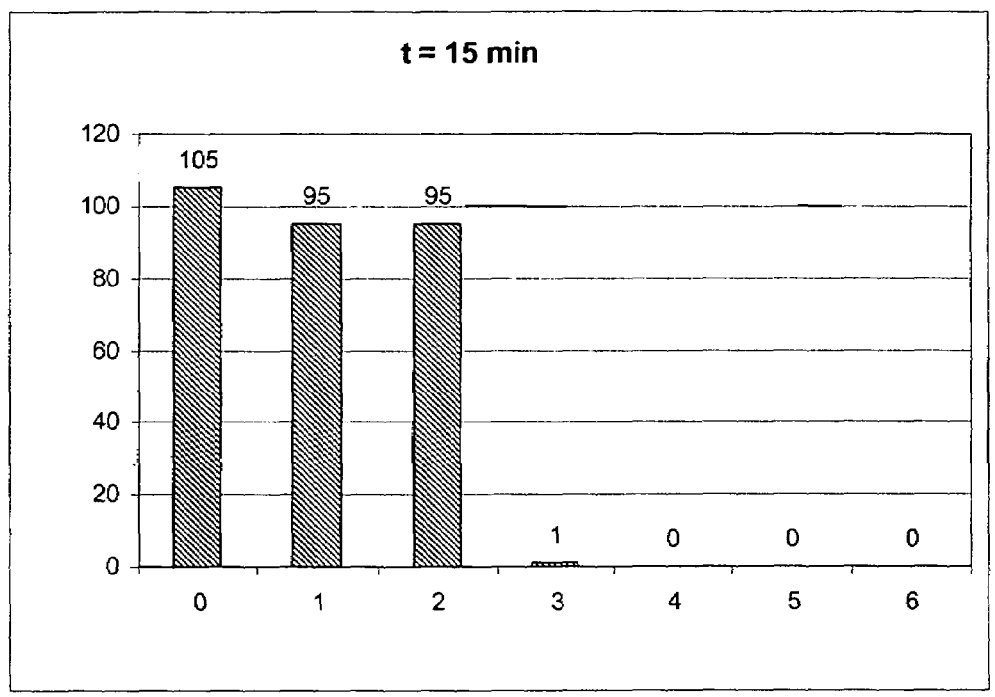
FIG. 2 Activity of proteinase K at t=15 min in relation to varying concentrations of guanidinium thiocyanate (15 min values). The x axis indicates the molar concentration of guanidinium thiocyanate, the y axis indicates the activity of proteinase K in [%].
Figure 3:
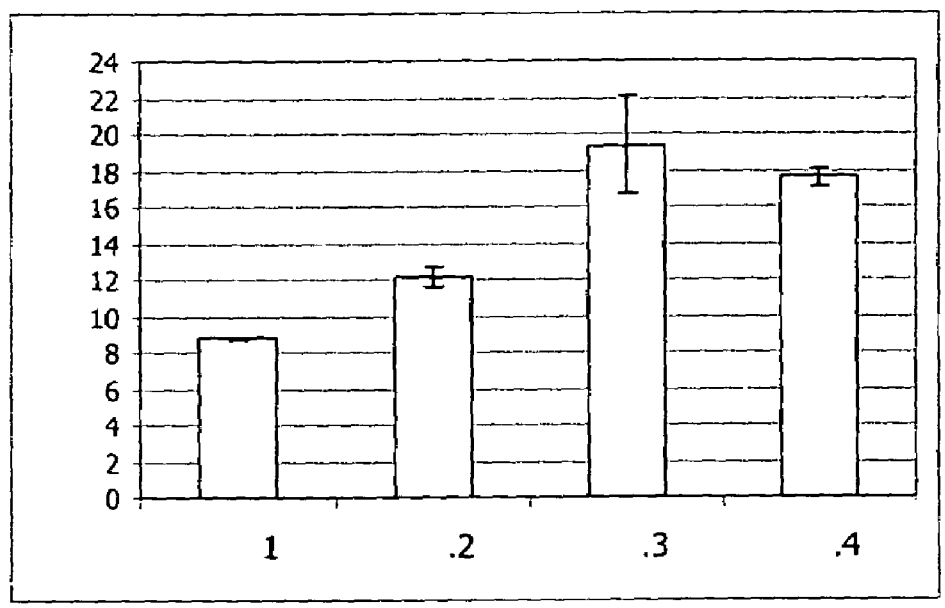
FIG. 3 Yield of DNA in μg per ml blood, according to Example 2 and Table 3. The x axis indicates the respective experiment, the y axis indicates the DNA yield in μg per ml blood. Also indicated are the standard deviations.
Figure 4:
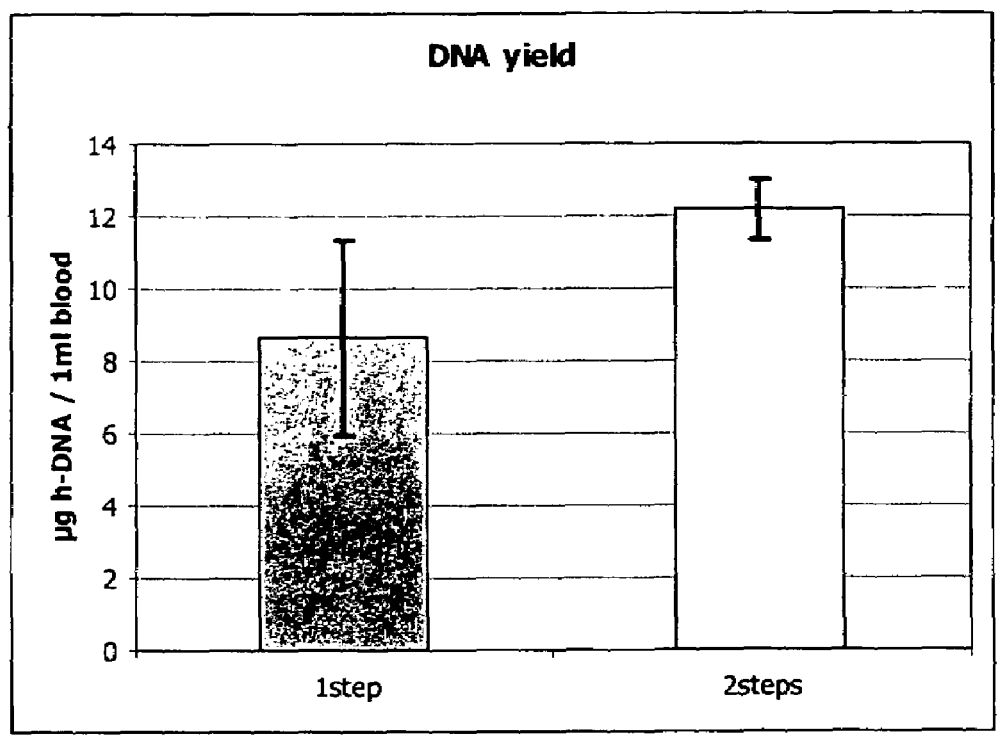
FIG. 4 Yield of DNA in μg per ml blood, according to Example 3 and Table 5. The x axis indicates the respective experiment, the y axis indicates the DNA yield in μg per ml blood. Also indicated are the standard deviations.
Figure 5:
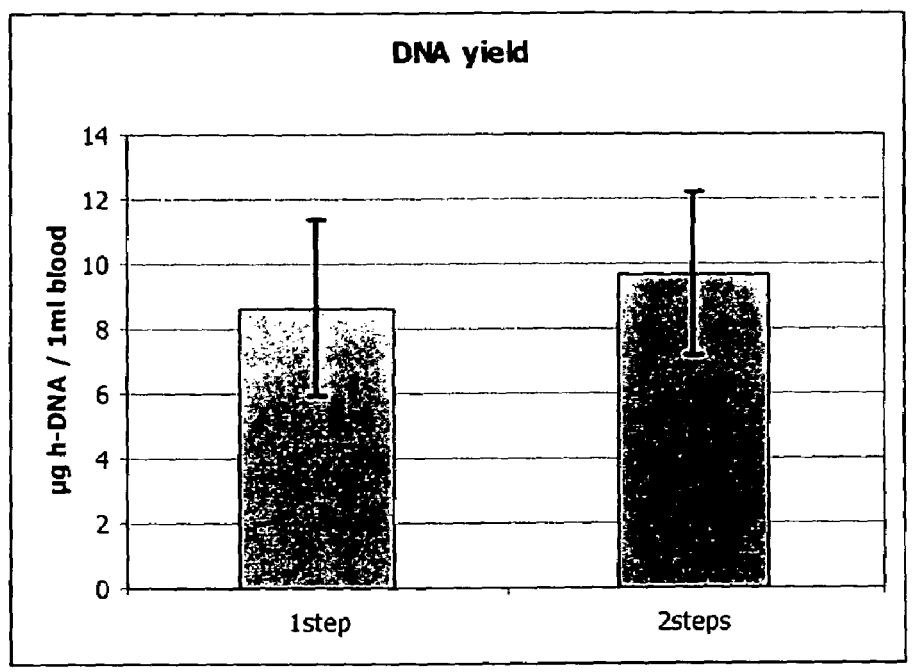
FIG. 5 Yield of DNA in μg per ml blood, according to Example 4 and Table 7. The x axis indicates the respective experiment, the y axis indicates the DNA yield in μg per ml blood. Also indicated are the standard deviations.

Table 1 lists the 0 min values of the activity of proteinase K in the presence of guanidinium thiocyanate at the different concentrations given in (A). Table 2 lists the 15 min values of the activity of proteinase K in the presence of guanidinium thiocyanate at the different concentrations given in (A) as well as the control value (no chaotropic agent present). The values are expressed in relation to the 0 min activity value of proteinase K in the control buffer without chaotropic agent (see (A)), corresponding to 0.5 U/ml; this value was set as 100%. The data of Table 1 and Table 2 are graphically represented in FIG. 1 and FIG. 2.

TABLE 1

Activity of proteinase K at t = 0 min in relation to varying concentrations of guanidinium thiocyanate (0 min values)

| concentration [M] | Activity [%] |
| --- | --- |
| 0 | 81 |
| 1 | 94 |
| 2 | 100 |
| 3 | 66 |
| 4 | 1 |
| 5 | 0 |
| 6 | 0 |

TABLE 2

Activity of proteinase K at t = 15 min in relation to varying concentrations of guanidinium thiocyanate (15 min values)

| concentration [M] | Activity [%] |
| --- | --- |
| 0 | 105 |
| 1 | 95 |
| 2 | 95 |
| 3 | 1 |
| 4 | 0 |
| 5 | 0 |
| 6 | 0 |

EXAMPLE 2

(A) Reagents
  a) proteinase K stock solution: recombinant proteinase K, PCR grade, 50 U/ml
  b) Lysis Buffer: 4 M guanidinium thiocyanate, 50 mM Tris-HCl, 20% TRITON X-100, pH 6.0
  c) Binding Buffer: 4 M guanidinium thiocyanate, 50 mM Tris-HCl, 20% TRITON X-100, pH 6.0
  d) Inhibitor Removal Buffer: 5 M guanidinium hydrochloride, 20 mM Tris-HCl, 38% ethanol, pH 6.6
  e) Wash Buffer: 20 mM NaCl, 2 mM Tris-HCl, 80% ethanol, pH 7.5
  f) Elution Buffer: 50 mM Tris-HCl, pH 8.2
  g) Ethanol (100%)

Additionally necessary: Commercially available spin columns containing a silica membrane, e.g. NucleoSpin Blood L, distributed by Machery & Nagel.

(B) Experiment 1: One-Step Procedure without Proteinase K Treatment
1. pipette 1,000 μl EDTA blood into a 15 ml Falcon tube
2. add 1,000 μl Lysis Buffer, vortex gently
3. incubate for 15 min at room temperature on a roller mixer, agitate
4. put a spin column in a new Falcon tube
5. transfer the mixture of steps 1.-2. (about 2,000 μl) to the spin column
6. centrifuge for 3 min at 1,900×g.

7. add 1,000 µl Inhibitor Removal Buffer
8. centrifuge for 2 min at 4,500×g.
9. add 2,000 µl Wash Buffer
10. centrifuge for 10 min at 4,500×g.
11. discard flowthrough and put filter column in a new Falcon tube
12. elute with 300 µl pre-heated (70° C.) Elution Buffer
13. incubate for 5 min at room temperature
14. centrifuge for 2 min at 4,500×g.
15. OD measurement of the eluate at 260, 280 and 320 nm (C) Experiment 2: One-Step Procedure Including Proteinase K Treatment
1. pipette 125 µl proteinase K into a 15 ml Falcon tube
2. add 1,000 µl EDTA blood, vortex gently
3. add 1,000 µl Lysis Buffer, vortex gently
4. incubate and shake at 56° C. for 15 min (e.g. by using a thermomixer), agitate
5. put a spin column in a new Falcon tube
6. transfer the mixture of steps 1.-3. (about 2,125 µl) to the spin column
7. centrifuge for 3 min at 1,900×g
8. add 1,000 µl Inhibitor Removal Buffer
9. centrifuge for 2 min at 4,500×g
10. add 2,000 µl Wash Buffer
11. centrifuge for 10 min at 4,500×g.
12. discard flowthrough and put filter column in a new Falcon tube
13. eluate with 300 µl pre-heated (70° C.) Elution Buffer
14. incubate for 5 min at room temperature
15. centrifuge for 2 min at 4,500×g.
16. OD measurement of the eluate at 260, 280 and 320 nm (D) Experiment 3: Two-Step Procedure Including Ethanol
1. pipette 125 µl proteinase K into a 15 ml Falcon tube
2. add 1,000 µl EDTA blood, vortex gently
3. add 1,000 µl Lysis Buffer, vortex gently
4. incubate and shake at 56° C. for 15 min (e.g. by using a thermomixer), agitate
5. add 1,000 µl Ethanol, vortex gently
6. put a spin column in a new Falcon tube
7. transfer the mixture of steps 1.-5. (about 3,125 µl) to the spin column
8. centrifuge for 3 min at 1,900×g.
9. add 1,000 µl Inhibitor Removal Buffer
10. centrifuge for 2 min at 4,500×g
11. add 2,000 µl Wash Buffer
12. centrifuge for 10 min at 4,500×g
13. discard flowthrough and put filter column on a new Falcon tube
14. eluate with 300 µl pre-heated (70° C.) Elution Buffer
15. incubate for 5 min at room temperature
16. centrifuge for 2 min at 4,500×g.
17. OD measurement of the eluate at 260, 280 and 320 nm (E) Experiment 4: Two-Step Procedure Including Binding Buffer
1. pipette 125 µl proteinase K into a 15 ml Falcon tube
2. add 1,000 µl EDTA blood, vortex gently
3. add 1,000 µl Lysis Buffer, vortex gently
4. incubate and shake at 56° C. for 15 min (e.g. by using a thermomixer), agitate
5. add 1,000 µl Binding Buffer, vortex gently
6. put a spin column in a new Falcon tube
7. transfer the mixture of the steps 1.-5. (about 3,125 µl) to the spin column
8. centrifuge for 3 min at 1,900×g
9. add 1,000 µl Inhibitor Removal Buffer
10. centrifuge for 2 min at 4,500×g.
11. add 2,000 µl Wash Buffer
12. centrifuge for 10 min at 4,500×g.
13. discard flowthrough and put filter column on a new Falcon tube
14. eluate with 300 µl pre-heated (70° C.) Elution Buffer
15. incubate for 5 min at room temperature
16. centrifuge for 2 min at 4,500×g.
17. OD measurement of the eluate at 260, 280 and 320 nm

TABLE 3

Yield of human DNA, in [µg/ml blood]

| | Experiment 1 | Experiment 2 | Experiment 3 | Experiment 4 |
|---|---|---|---|---|
| (a) | 8.72 | 11.78 | 21.23 | 17.96 |
| (b) | 8.81 | 12.57 | 17.43 | 17.30 |
| Mean | 8.77 | 12.18 | 19.33 | 17.63 |
| SD | 0.06 | 0.55 | 2.68 | 0.46 |

(a) and (b) indicate data from replicate experiments;
SD: standard deviation

TABLE 4

DNA purity as determined by 260 nm/280 nm ratios with 320 nm correction

| | Experiment 1 | Experiment 2 | Experiment 3 | Experiment 4 |
|---|---|---|---|---|
| (a) | 1.95 | 1.92 | 1.87 | 1.88 |
| (b) | 1.96 | 1.85 | 1.88 | 1.84 |

(a) and (b) indicate data from replicate experiments (see Table 3)

With regard to purity of DNA, a 260 nm/280 nm ratio (including 320 nm correction) of 1.8±0.1 is regarded as being acceptable. The data show that the method according to the invention, that is to say the method of Experiment 4 produces equally pure (if not a DNA of higher purity) compared with the the method of Experiment 3.

EXAMPLE 3

(A) Reagents
a) Lysis buffer/binding Buffer, chaotropic (7M [lysis buffer]/4M [binding buffer] guanidinium thiocyanate, 50 mM Tris-HCl, 20% TRITON X-100, pH 6.0)
b) Inhibitor Removal Buffer (5M guanidinium HCl, 20 mM Tris-HCl, 38% ethanol, pH 6.6)
c) Washing Buffer (20 mM NaCl, 2 mM Tris-HCl, 80% ethanol, pH 7.5)
d) Elution Buffer (50 mM Tris, pH 8.1)
e) Ethanol (absolute)

Additionally necessary: Glass fibre filter columns (with silica membrane, e.g. NucleoSpin Blood L, commercially available from Macherey-Nagel)

(B) Experiment 5, One-Step Procedure: Lysis Buffer: 7M, No Binding Buffer 1,000 µl EDTA blood was pipetted into a 15 ml Falcon tube, 1,000 µl Lysis buffer (7 M) was added and the tube was vortexed. The mixture was incubated for 15 min at 56° C. on a Thermo Mixer. A new Falcon tube with a glass fibre filter column was provided and the whole sample preparation (about 2,000 µl; chaotrope concentration 3.5 M) was transferred to the filter column. After centrifugation at 1,900×g for 3 min 1,000 µl Inhibitor Removal Buffer was transferred to the column, followed by another centrifugation step at 4,200×g for 2 min. After that, 2,000 μl Washing Buffer was transferred to the column, followed by centrifugation at 4,200×g for 10 min. The flowthrough was discarded and the filter column was put on a new Falcon tube. Bound nucleic acids were eluted using 500 μl pre-heated (70° C.) Elution Buffer. The Elution Buffer was transferred to the column and incubated for 5 min at room temperature. After centrifugation at 4,200×g for 2 min the flowthrough was analyzed by optical density measurement at 230, 260, 280 and 320 nm.

(C) Experiment 6, Two-Step Procedure: Lysis Buffer: 7M, Binding Buffer: 4M 1,000 μl EDTA blood was pipetted into a 15 ml Falcon tube, 1,000 μl Lysis buffer (7 M) was added and the tube was vortexed. The mixture was incubated for 15 min at 56° C. on a Thermo Mixer. 500 μl Binding Buffer (4 M) was added mixed by vortexing. A new Falcon tube with a glass fibre filter column was provided and the whole sample preparation (about 2,500 μl; chaotrope concentration 4.5 M) was transferred to the filter column. After centrifugation at 1,900×g for 3 min 1,000 μl Inhibitor Removal Buffer was transferred to the column, followed by another centrifugation step at 4,200×g for 2 min. After that, 2,000 μl Washing Buffer was transferred to the column, followed by centrifugation at 4,200×g for 10 min. The flowthrough was discarded and the filter column was put on a new Falcon tube. Bound nucleic acids were eluted using 500 μl pre-heated (70° C.) Elution Buffer. The Elution Buffer was transferred to the column and incubated for 5 min at room temperature. After centrifugation at 4,200×g for 2 min the flowthrough was analyzed by optical density measurement at 230, 260, 280 and 320 nm.

TABLE 5

Yield of human DNA, in [μg/ml blood]

|     | Experiment 5 | Experiment 6 |
|-----|--------------|--------------|
| (a) | 5.95         | 11.35        |
| (b) | 11.35        | 13.02        |
| Mean| 8.65         | 12.18        |
| SD  | 3.82         | 1.18         |

(a) and (b) indicate data from replicate experiments;
SD: standard deviation

TABLE 6

DNA purity as determined by 260 nm/280 nm ratios with 320 nm correction

|      | Experiment 5 | Experiment 6 |
|------|--------------|--------------|
| (a)  | 1.92         | 1.94         |
| (b)  | 1.88         | 1.81         |
| mean | 1.90         | 1.88         |

(a) and (b) indicate data from replicate experiments (see Table 5)

EXAMPLE 4

(A) Reagents
a) Lysis buffer/binding Buffer, chaotropic (7M [lysis buffer]/5M [lysis buffer]/4M [binding buffer] guanidinium thiocyanate, 50 mM Tris-HCl, 20% TRITON X-100, pH 6.0)
b) Inhibitor Removal Buffer (5M guanidinium HCl, 20 mM Tris-HCl, 38% ethanol, pH 6.6)
c) Washing Buffer (20 mM NaCl, 2 mM Tris-HCl, 80% ethanol, pH 7.5)
d) Elution Buffer (50 mM Tris, pH 8.1)
e) Ethanol (absolute)

Additionally necessary: Glass fibre filter columns (with silica membrane, e.g. NucleoSpin Blood L, commercially available from Macherey-Nagel)

(B) Experiment 7, One-Step Procedure: Lysis Buffer: 7M, No Binding Buffer 1,000 μl EDTA blood was pipetted into a 15 ml Falcon tube, 1,000 μl Lysis buffer (7 M) was added and the tube was vortexed. The mixture was incubated for 15 min at 56° C. on a Thermo Mixer. A new Falcon tube with a glass fibre filter column was provided and the whole sample preparation (about 2,000 μl; chaotrope concentration 3.5 M) was transferred to the filter column. After centrifugation at 1,900×g for 3 min 1,000 μl Inhibitor Removal Buffer was transferred to the column, followed by another centrifugation step at 4,200×g for 2 min. After that, 2,000 μl Washing Buffer was transferred to the column, followed by centrifugation at 4,200×g for 10 min. The flowthrough was discarded and the filter column was put on a new Falcon tube. Bound nucleic acids were eluted using 500 μl pre-heated (70° C.) Elution Buffer. The Elution Buffer was transferred to the column and incubated for 5 min at room temperature. After centrifugation at 4,200×g for 2 min the flowthrough was analyzed by optical density measurement at 230, 260, 280 and 320 nm.

(C) Experiment 8, Two-Step Procedure: Lysis Buffer: 5M, Binding Buffer: 4M 1,000 μl EDTA blood was pipetted into a 15 ml Falcon tube, 1,000 μl Lysis buffer (5 M) was added and the tube was vortexed. The mixture was incubated for 15 min at 56° C. on a Thermo Mixer. 500 μl Binding Buffer (4 M) was added mixed by vortexing. A new Falcon tube with a glass fibre filter column was provided and the whole sample preparation (about 2,500 μl; chaotrope concentration 3.5 M) was transferred to the filter column. After centrifugation at 1,900×g for 3 min 1,000 μl Inhibitor Removal Buffer was transferred to the column, followed by another centrifugation step at 4,200×g for 2 min. After that, 2,000 μl Washing Buffer was transferred to the column, followed by centrifugation at 4,200×g for 10 min. The flowthrough was discarded and the filter column was put on a new Falcon tube. Bound nucleic acids were eluted using 500 μl pre-heated (70° C.) Elution Buffer. The Elution Buffer was transferred to the column and incubated for 5 min at room temperature. After centrifugation at 4,200×g for 2 min the flowthrough was analyzed by optical density measurement at 230, 260, 280 and 320 nm.

TABLE 7

Yield of human DNA, in [μg/ml blood]

|      | Experiment 7 | Experiment 8 |
|------|--------------|--------------|
| (a)  | 5.95         | 7.16         |
| (b)  | 11.35        | 12.20        |
| Mean | 8.65         | 9.68         |
| SD   | 3.82         | 3.57         |

(a) and (b) indicate data from replicate experiments;
SD: standard deviation

TABLE 8

| | DNA purity as determined by 260 nm/280 nm ratios with 320 nm correction | |
|---|---|---|
| | Experiment 7 | Experiment 8 |
| (a) | 1.92 | 1.91 |
| (b) | 1.88 | 1.92 |
| mean | 1.90 | 1.92 |

(a) and (b) indicate data from replicate experiments (see Table 7)

What is claimed is:

1. A method for adsorbing a nucleic acid from a biological sample to a solid phase, comprising the steps of
providing an aqueous lysis buffer that contains a chaotropic agent;
mixing the lysis buffer with the biological sample, whereby the concentration of the chaotropic agent in the mixture is between 1 M and 4 M, and incubating the mixture;
dissolving an additional amount of chaotropic agent in or adding an aqueous solution containing additional chaotropic agent to the mixture of step (b), thereby increasing the concentration of the chaotropic agent in the mixture by more than 0.5 M; and
contacting the mixture of step (c) with the solid phase, thereby adsorbing the nucleic acid from the mixture to the solid phase,
wherein alcohol is not used to effectuate the adsorption.

2. The method of claim 1 wherein the chaotropic agent is selected from the group consisting of guanidinium hydrochloride, guanidinium thiocyanate, guanidinium isothiocyanate, an alkali iodide, and an alkali perchlorate.

3. The method of claim 1 wherein the lysis buffer of step (a) contains an enzyme with proteolytic activity.

4. The method of claim 3 wherein the enzyme with proteolytic activity is selected from the group consisting of a caspase, proteinase K, pronase E, esperase, and subtilisin.

5. The method of claim 1 wherein the lysis buffer of step (a) contains a detergent.

6. The method of claim 5 wherein the detergent in the lysis buffer of step (a) is selected from the group consisting of sodium dodecyl sulfate, lithium dodecyl sulfate, cetyltrimethylammoniumbromide, deoxycholic acid, sodium lauroyl sarcosine, TRITON X-100, TWEEN 20, octyl beta-D-glucoside, Nonidet P40, CHAPS, and Sulphobetaine 14.

7. The method of claim 1 wherein the solid phase comprises a porous or non-porous mineral substrate selected from the group consisting of silica gel, glass fibers, quartz fibers, and zeolites.

8. The method of claim 1 wherein the solid phase comprises magnetic glass particles.

9. A method to isolate a nucleic acid from a biological sample comprising the steps of
(a) providing an aqueous lysis buffer that contains a chaotropic agent;
(b) mixing the lysis buffer with the biological sample, whereby the concentration of the chaotropic agent in the mixture is between 1 M and 4 M, and incubating the mixture;
(c) dissolving an additional amount of chaotropic agent in or adding an aqueous solution containing additional chaotropic agent to the mixture of step (b), thereby increasing the concentration of the chaotropic agent in the mixture by more than 0.5 M;
(d) providing a solid phase and contacting the mixture of step (c) with the solid phase, thereby adsorbing the nucleic acid from the mixture to the solid phase;
(e) separating the solid phase from the liquid phase; and
(f) eluting the nucleic acid from the solid phase thereby isolating the nucleic acid, wherein alcohol is not used to effectuate the adsorption.

10. The method of claim 9 wherein the chaotropic agent is selected from the group consisting of guanidinium hydrochloride, guanidinium thiocyanate, guanidinium isothiocyanate, an alkali iodide, and an alkali perchlorate.

11. The method of claim 9 wherein the lysis buffer of step (a) further contains an enzyme with proteolytic activity and a detergent.

12. The method of claim 11 wherein the enzyme with proteolytic activity is selected from the group consisting of a caspase, proteinase K, pronase E, esperase, and subtilisin, and the detergent is selected from the group consisting of sodium dodecyl sulfate, lithium dodecyl sulfate, cetyltrimethylammoniumbromide, deoxycholic acid, sodium lauroyl sarcosine, TRITON X-100, TWEEN 20, octyl beta-D-glucoside, Nonidet P40, CHAPS, and Sulphobetaine 14.

13. The method of claim 12 wherein the mixture of step (b) contains the biological sample, guanidinium thiocyanate at a concentration of about 2 M, Tris salt at a concentration of about 25 mM, TRITON X-100 at a concentration of about 10% volume by volume, and proteinase K, wherein the proteolytic activity of proteinase K in the mixture is about 3 U/ml and wherein the pH of the mixture is about 6.

14. The method of claim 12 wherein the mixture of step (b) contains the biological sample, guanidinium hydrochloride at a concentration of about 2.7 M, urea at a concentration of about 5 mM, Tris salt at a concentration of about 5 mM, TRITON X-100 at a concentration of about 9% volume by volume, and proteinase K, wherein the proteolytic activity of proteinase K in the mixture is about 3 U/ml and wherein the pH of the mixture is between 4.4 and 6.5.

15. The method of claim 12 wherein the mixture of step (b) contains the biological sample, guanidinium hydrochloride at a concentration of about 2.4 M, urea at a concentration of about 1.6 mM, Tris salt at a concentration of about 85 mM, EDTA at a concentration of about 88 mM, NaCl at a concentration of about 8 mM, TRITON X-100 at a concentration of about 9% volume by volume, and proteinase K, wherein the proteolytic activity of proteinase K in the mixture is about 3 U/ml and wherein the pH of the mixture is between 4.4 and 6.5.

16. The method of claim 13 wherein the mixture of step (b) is incubated for 10 min to 30 min at a temperature between about 20° C. and about 75° C.

17. The method of claim 9 wherein the solid phase comprises a porous or non-porous mineral substrate selected from the group consisting of silica gel, glass fibers, quartz fibers, and zeolites.

18. The method of claim 9 wherein the solid phase comprises magnetic glass particles.

19. The method of claim 9 wherein the biological sample comprises bacterial cells, eukaryotic cells, viruses or mixtures thereof.

* * * * *